(12) United States Patent
Songer et al.

(10) Patent No.: US 6,682,561 B2
(45) Date of Patent: Jan. 27, 2004

(54) SPINAL FIXATION SYSTEM

(75) Inventors: Matthew N. Songer, Marquette, MI (US); Jeffrey D. Vlahos, Bruce Crossing, MI (US); Thomas S. Kilpela, Marquette, MI (US)

(73) Assignee: Pioneer Laboratories, Inc., Marquette, MI (US)

( * ) Notice: Subject to any disclaimer, the term of this patent is extended or adjusted under 35 U.S.C. 154(b) by 0 days.

(21) Appl. No.: 10/104,487

(22) Filed: Mar. 25, 2002

(65) Prior Publication Data

US 2002/0169508 A1 Nov. 14, 2002

Related U.S. Application Data

(63) Continuation-in-part of application No. 09/561,248, filed on Apr. 27, 2000, now Pat. No. 6,395,030, which is a continuation-in-part of application No. 09/099,310, filed on Jun. 18, 1998, now abandoned.

(51) Int. Cl.[7] .................................................. A61F 2/44
(52) U.S. Cl. .................................. 623/17.11; 623/16.11
(58) Field of Search .......................... 623/17.11, 17.15, 623/17.16, 16.11

(56) References Cited

U.S. PATENT DOCUMENTS

| 4,289,123 A | 9/1981 | Dunn |
|---|---|---|
| 4,401,112 A | 8/1983 | Rezaian |
| 4,554,914 A | 11/1985 | Kapp et al. |
| 4,599,086 A | 7/1986 | Doty |
| 4,636,217 A | 1/1987 | Ogilvie et al. |
| 4,743,256 A | 5/1988 | Brantigan |
| 4,759,769 A | 7/1988 | Hedman et al. |
| 4,892,545 A | 1/1990 | Day et al. |
| 5,059,193 A | 10/1991 | Kuslich |
| 5,147,360 A | 9/1992 | Dubousset |
| 5,147,363 A | 9/1992 | Harle |
| 5,192,327 A | 3/1993 | Brantigan |
| 5,261,911 A | 11/1993 | Carl |
| 5,304,210 A | 4/1994 | Crook |
| 5,306,307 A | 4/1994 | Senter et al. |
| 5,306,309 A | 4/1994 | Wagner et al. |
| 5,360,430 A | 11/1994 | Lin |
| 5,425,773 A | 6/1995 | Boyd et al. |
| 5,458,641 A | 10/1995 | Ramirez Jimenez |
| 5,556,431 A | 9/1996 | Buttner-Janz |
| 5,591,235 A | 1/1997 | Kuslich |
| 5,603,713 A | 2/1997 | Aust et al. |

(List continued on next page.)

FOREIGN PATENT DOCUMENTS

EP 0 374 088 * 12/1988 ........... A61B/17/58

OTHER PUBLICATIONS

Article from Chapter 19/Application of Rezaian Anterior Fixation System by S.M. Rezaian, "Application of Rezaian Anterior Fixation System for the Management of Fractures of Thoracolumbar Spine", pp. 193–199.

(List continued on next page.)

Primary Examiner—David H. Willse
Assistant Examiner—Thomas Barrett
(74) Attorney, Agent, or Firm—Garrettson Ellis Seyfarth Shaw

(57) ABSTRACT

An implantable, spinal, vertebral replacement device comprises a tubular cage for fitting into a space left by a missing vertebral body and for optionally retaining bone graft material. First and second transverse plates are respectively positioned at opposed ends of the tubular cage for supporting the respective cage ends and for pressing a plate face against an adjacent vertebral body in spinal column-supporting relation. The transverse plates are each joined in transverse relation to a vertebral attachment plate which, in use, extends generally parallel to the spine. The vertebral attachment plate defines screw holes for preferably open helix screw securance to the pair of adjacent vertebral bodies that bracket the space left by the missing vertebral body.

16 Claims, 3 Drawing Sheets

U.S. PATENT DOCUMENTS

| | | | |
|---|---|---|---|
| 5,662,683 A | * 9/1997 | Kay | 606/232 |
| 5,674,296 A | 10/1997 | Bryan et al. | |
| 5,702,453 A | * 12/1997 | Rabbe et al. | 623/17 |
| 5,755,796 A | 5/1998 | Ibo et al. | |
| 5,888,223 A | 3/1999 | Bray, Jr. | |
| 5,916,267 A | * 6/1999 | Tienboon | 623/17.11 |
| 6,106,557 A | * 8/2000 | Robioneck et al. | 623/17.15 |
| 6,190,413 B1 | * 2/2001 | Sutcliffe | 623/17.11 |

OTHER PUBLICATIONS

Article from: AcroMed Surgeon–driven spinal solutions: "Thoracolumbar Trauma & Tumor" dated Jul. 1995; 12 pages.

Article from: Acromed The Leader in spinal technology: "Kaneda SR (Smooth Rod) Anterior Spinal System, Titanium", 1994, AcroMed Corporation, 6 pages.

Article from: AcroMed The leader in Spinal technology: University AM Plate Titanium Anterior System, AcroMed Corporation 9/94, 5 pages.

Article from: 43rd Annual Meeting, Orthopaedic Research Society, Feb. 9–13, 1997, pp. 382: "Comparative Kinematics of a collapsible and Rigid Anterior Devices" by Goel et al., Iowa Spine Research Center, University of Iowa.

Article from: SPINE vol. 22, No. 6, pp 686–690, 1997, Lippincott–Raven Publishers,"Anterolateral Dynamized Instrumentation and Fusion for Unstable Thoracolumbar and Lumbar Burst Fractures" by Carl et al.

SPINE vol. 23, No. 5, pp. 543–550, Article: "Stability Potential of Spinal Instrumentations in Tumor Vertebral Body Replacement Surgery" by Vahldiek et al, 1998.

Article by Edmund T. Dombrowski, Jr. MD: "Rezaian Fixator in the Anterior Stabilization of Unstable Spine" from Orthopaedic Review Vo. XV, No. 1, Jan., 1986, pp. 30–34.

* cited by examiner

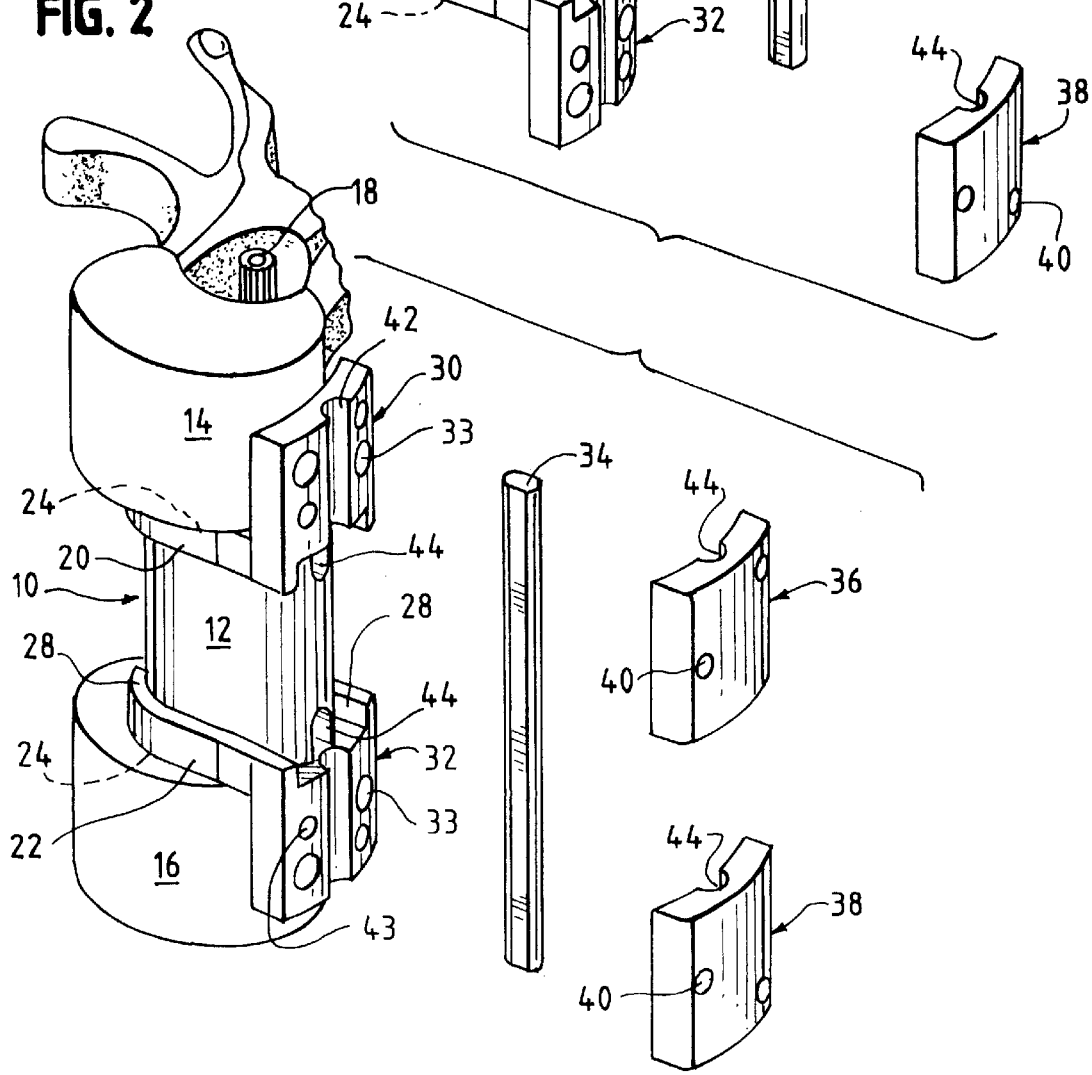

SPINAL FIXATION SYSTEM

CROSS REFERENCE TO RELATED APPLICATION

This is a continuation-in-part of Songer et al. U.S. application Ser. No. 09/561,248, filed Apr. 27, 2000, now U.S. Pat. No. 6,395,030B1 which is a continuation-in-part of Songer et al. U.S. application Ser. No. 09/099,310, filed Jun. 18, 1998, now abandoned.

BACKGROUND OF THE INVENTION

There are various devices and techniques for reconstructing the anterior spinal column in the lumbar or thoracic spine. Specifically, a bone graft may be inserted between the vertebrae. The spine is then fused posteriorly with an implantable instrument of various designs.

However, the bone graft usually was obtained from the fibula or the iliac crest. Problems have arisen with donor site morbidity.

Also, various implantable devices for reconstruction of the spine comprise anterior plate and/or anterior rod systems.

Typically, one of two methods are used to reconstruct the anterior spine. Either an autologous bone graft or an allograft is inserted into the defect, and a plate system is applied to the lateral side of the spine. Alternatively, a tubular "cage" may be inserted between vertebral bodies, and a plate may be applied, extending between intact vertebral bodies on either side of the defect. The cage may be filled with bone graft material such as bone fragments. The cage retains the material in place while the bone graft grows, fusing the two adjacent vertebral bodies.

By this invention, an integral, modular device is provided to replace a vertebral body that has been destroyed or must be removed because of fracture, tumor, infection or the like, while the device of this invention provides a site for an effective bone graft to fuse with intact, adjacent vertebral bodies, with both the device and the optional bone graft extending between the adjacent vertebral bodies and across the original space of the missing vertebral body. Also an improved technique of fastening the device in place is provided by this invention.

DESCRIPTION OF THE INVENTION

By this invention, an implantable, spinal, vertebral replacement device is provided. The device comprises a tubular cage for fitting into a space of a missing or damaged vertebral body. This tubular cage may be made of any implantable biomaterial such as stainless steel alloy, titanium, carbon fiber composite, bone, or the like, and can be used if desired to retain bone graft material in a desired position between intact vertebral bodies to form a fusion between the intact vertebral bodies across the site of the missing vertebral body. First and second transverse plates are respectively positioned at opposed ends of the tubular cage for supporting the respective ends of the tubular cage, and for pressing a plate face against an adjacent vertebral body in spinal column-supporting relation.

The transverse plates are each joined in transverse relation to typically a single vertebral attachment plate. This latter plate, in use, extends generally parallel to the spine, with the vertebral attachment plate defining screw holes for screw securance to at least one vertebral body adjacent to the space of the missing vertebral body.

Accordingly, by this invention both support and spacing of adjacent vertebral bodies is provided, along with retention and positioning of a tubular cage, which can retain bone graft material for the future growth of a strong bone graft after surgery.

In one embodiment, each transverse plate may be joined to a separate vertebral attachment plate, for attachment of the vertebral attachment plate to a separate, adjacent vertebral body positioned on an opposed side of the space left by the missing vertebral body. Cover plates may be carried on the vertebral attachment plate to cover the screw holes for screw securance to a vertebral body, and to also cover the screws occupying those holes. Thus, backing out of the screws in the holes after implantation of the device can be suppressed by the presence of such a cover plate.

As stated, the spinal replacement device of this invention may utilize a single vertebral attachment plate, to which both transverse plates are attached, with the vertebral attachment plate having screw holes for attachment to both of the adjacent, vertebral bodies.

As a further feature of this invention, the transverse plates may each have a peripheral, upstanding wall to surround and retain a respective supported end of the cage to prevent lateral cage movement. The peripheral, upstanding wall and cage are respectively dimensioned to preferably cause tight retention of the cage. The peripheral upstanding wall is preferably open at one end of the transverse plate, preferably the end facing the vertebral attachment plate, to receive the cage with lateral motion relative to the spinal column, this specific embodiment is particularly used with the system having the pair of vertebral attachment plates. Such a system can be used with cages of varying length, which slide into engagement with the peripheral, upstanding walls of the transverse plates.

Preferably, each transverse wall has a roughened face that faces the adjacent, intact vertebral body against which it presses in use. The roughened face may comprise a titanium mesh coating secured to the face of the plate that engages an end of the adjacent vertebral body, or it may be prepared by a variety of other, known techniques.

Also, each transverse plate preferably defines a central aperture, so that communication is available between the intact vertebral bodies and the bone graft material within the cage.

Some adjustability can be provided to the embodiment having a single vertebral attachment plate by providing the transverse plates with a hinged connection with the vertebral attachment plate, or even a frictional, spring-pinching connection between two flat surfaces of each transverse plate, respectively engaging opposed side surfaces of the vertebral attachment plate. Additionally, a bracket or strap may extend across an open end of the vertebral attachment plate with an aperture, for later application if desired after the cage has been positioned in the desired, surgical position, for better retention of each transverse plate with the vertebral attachment plate.

Preferably, the cage defines a slot at at least one end thereof, which slot is proportioned to receive a surgical distractor, for use during insertion of the cage into a position between the vertebral bodies.

Also, the cage may be elongated in one transverse dimension relative to its other transverse dimension, with the long dimension generally extending from side to side of the spine.

Accordingly, by the use of the above principles, a spinal replacement device is provided which can exhibit a unique combination of advantages, including a solid, firm retention of the entire system properly positioned in the spine, coupled with the facility to retain bone graft material in a position where growth can take place so that, after convalescence, the patient is less dependent upon the non-living implant, and more dependent on a more natural regrowth of bone in the spine.

As another aspect of the invention of this application, the spinal vertebral replacement device is advantageously secured to the intact vertebral bodies that are adjacent to the site of the missing vertebral body by means of screws that comprise an open, helical structure, generally in a manner similar to screws as disclosed by Kay U.S. Pat. No. 5,662,683 or European Patent Publication 0,374,088. These screws have some similarity to a simple corkscrew, being open at their center, rather than defining a metallic shaft in the manner of conventional screws. Several significant advantages are achieved when such a particular type of screw is used in combination with the spinal replacement device of this invention to secure the spinal replacement device to intact vertebrae. Among these advantages, as bone deflects, as can be expected in the spine of an active person, the open helix of such a screw better deflects with the bone, providing better load sharing over the length of the screw, to provide better screw fatigue life. As another advantage, an open helical screw does not require the previous removal of bone with a reaming drill, so that the screw does not displace a large plug of bone upon its insertion. Accordingly, much less bone is destroyed. Additionally, removal of the open, helical screw leaves only a narrow, elongated, helical path, whereas removal of an ordinary screw leaves a sizable hole in the bone, for significant weakening thereof.

Thus, since the open, helical screw destroys less bone upon insertion, a larger diameter, open helical screw can be used, when compared with a traditional bone screw. This larger diameter, open helical screw will have greater pull out strength, when compared with a corresponding, traditional bone screw positioned at the same site. It also may make possible in some circumstances the utilization of a single, open helical screw where otherwise two traditional bone screws would be necessary, with the result that substantially less bone is removed, and accordingly the vertebrae which receives the open, helical screw remains significantly stronger.

It may also be desired for a multiple shank open, helical screw to be used in accordance with this invention, where the screw comprises two or more independent, helical shanks which together define a central aperture, as disclosed, for example, in European Patent Publication 0,374,088.

DESCRIPTION OF THE DRAWINGS

In the drawings, FIG. 1 is an exploded, perspective view of the components of one embodiment of the spinal replacement device of this invention;

FIG. 2 is a perspective, partially assembled view of the spinal replacement device of FIG. 1, shown in the process of implantation in the spine to replace a missing vertebral body;

DESCRIPTION OF SPECIFIC EMBODIMENTS

Figure 3:
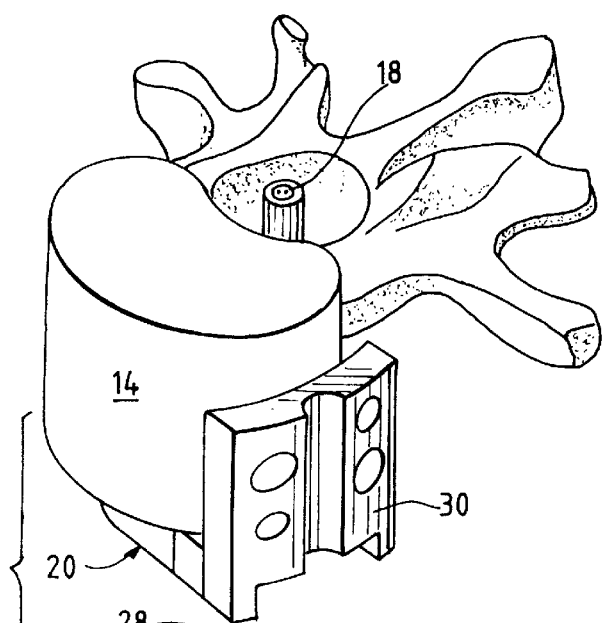
FIG. 3 is an enlarged, perspective view, with the cage deleted, of a portion of the system of FIG. 2, showing more details.

Referring to FIGS. 1–3, an implantable spinal vertebral replacement device is shown. Specifically, device 10 comprises a tubular cage 12 of oval cross section and made for example of titanium or a carbon fiber composite. Alternatively, cage 12 maybe made of a length of hollow bone typically having noncircular ends, cut to fit, and having a lumen that extends from end to end of the bone. Tubular cage 12 fits into the space which is left by a missing vertebral body which was either destroyed or had to be surgically removed, positioned between a pair of adjacent, intact vertebral bodies 14, 16 is as shown particularly in FIG. 2. It can be seen that the major transverse cross sectional axis of oval tubular cage 12 preferably extends from side to side of the spine comprising vertebra 14, 16. Cage 12 is positioned anterior to the spinal cord 18.

Cage 12 may be filled with bone fragments or other bone graft material so that, ultimately, an intact bone graft will be formed, extending between intact vertebra 14, 16.

First and second transverse plates 20, 22 are respectively positioned at opposed ends of tubular cage 12, for supporting the respective cage ends and for pressing a face 24 against an adjacent vertebral body 14 or 16 in spinal column-supporting relation. Transverse plates 20, 22 also define an aperture 26, but, typically, the face 24 that presses against the intact, vertebral bodies 14, 16 has more area than the area of each end of cage 12, so that a greater surface area pressing against each vertebral body 14, 16 is provided than would be provided by the mere presence of cage 12.

Also, transverse plates 22, 24 define a peripheral, upstanding wall 28, being dimensioned to cause tight retention of cage 12. Typically, wall 28 is open at one end of each transverse plate to receive the cage with lateral motion (relative to the spinal column). For example, in FIG. 2 it can be seen how cage 12 may enter the area circumscribed by upstanding walls 28 by advancement of transverse plates approximately from the right toward the cage, or by advancement of cage 12 toward the left into engagement with transverse plates 20, 22.

Transverse plates 20, 22 are each joined in transverse relation to at least one vertebral attachment plate. In the embodiment of FIGS. 1–3, a pair of such vertebral attachment plates 30, 32 are used. As shown, vertebral attachment plates 30, 32 extend generally parallel to the spine i.e. generally parallel to the line of vertebra 14, 16, being integrally secured in this embodiment in transverse relation, each to a separate transverse plate 20, 22. Also, each vertebral attachment plate 30, 32 defines first screw holes 33 for screw securance to one of the respective vertebral bodies 14, 16, as shown particularly in FIG. 2, for securance of the spinal vertebral replacement device in position.

In this embodiment, a rod 34 extends generally parallel to the spine and is retained between vertical attachment plates 30, 32 with a frictional pressure retention provided by cover plates 36, 38. Cover plates 36, 38 have screw holes 40 which mate with second screw holes 43 on the vertebral attachment plates 30, 32, for firm pressure attachment to provide a frictional pressure retention seal of rod 34 in the desired position. Also, cover plates 36, 38 serve to restrict and prevent unintended back-out of the bone screws from their retained position within screw holes 33 of the respective vertebral attachment plates 30, 32. Appropriate grooves 42, 44 are respectively provided in the vertebral attachment plates 30, 32 and the cover plates 36, 38 to appropriately receive rod 34.

Rod 34 may be cylindrical, but is preferably of non-circular cross section, to raise the torque resistance of the rod. For example, rod 34 may be of rectangular cross section with the major axis of the rectangle extending transversely from side-to-side of the spine in a direction generally parallel to the major cross-sectional axis of cage 12.

Cage 12 may define an end aperture 45 at each end on the long axis thereof, to provide access for a distractor tool, used in the surgical installation of the system.

Thus, an implantable anterial spinal fixator is provided, in which one or more vertebrae can be replaced with the device of this invention. The device firmly maintains the spacing of missing vertebrae, and also provides the capability for the firm retention and growth of a bone graft, to restore to the spine a more natural, strong regrowth of bone. The system is very flexible for use, and is capable of dimensional variations, for example by the use of varying lengths of the cage 12. If desired, transverse plates 20, 22 may be connected to vertebral attachment plates 30, 32 by a hinge, which provides added dimensional tolerance capability to the system.

Figure 4:
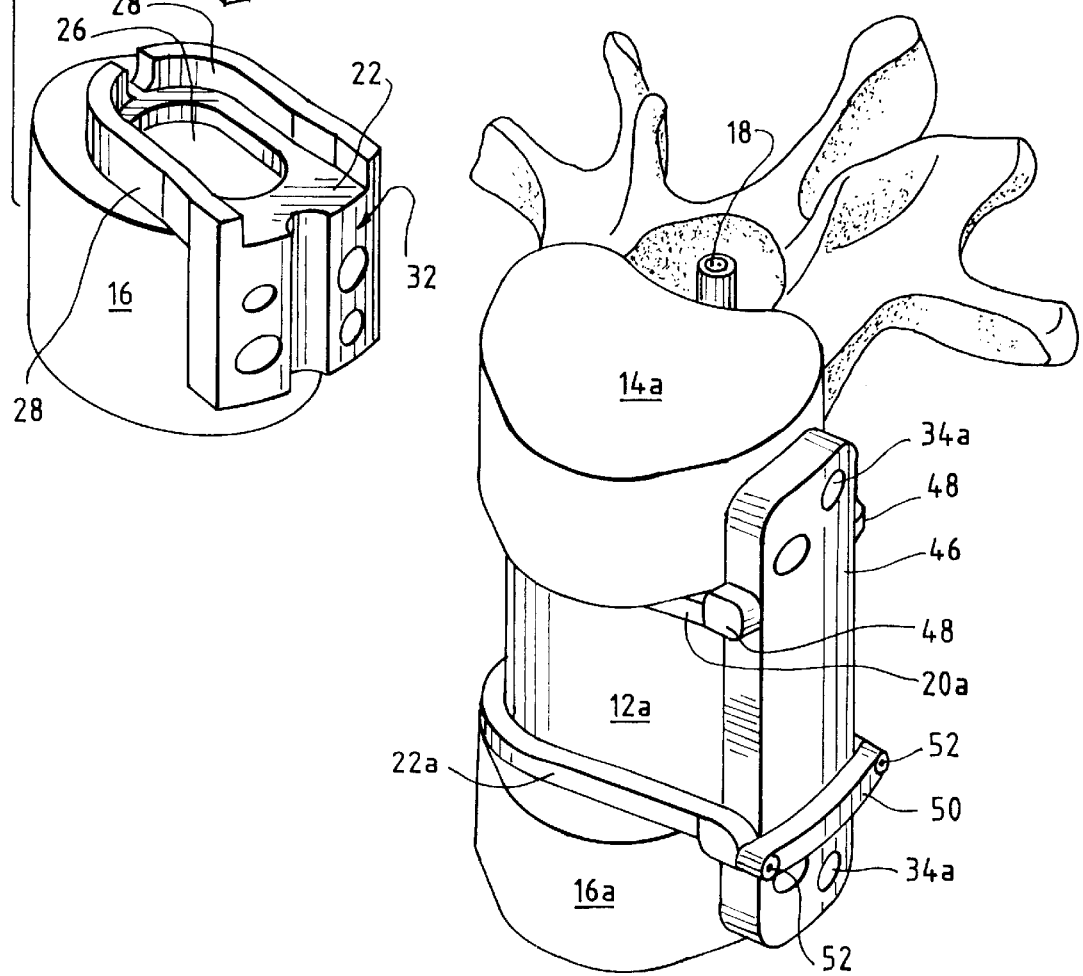
FIG. 4 is a perspective view showing a modified embodiment of the invention in fully implanted form in the spine, replacing a missing vertebral body.

Referring to FIG. 4, another embodiment of the implantable spinal vertebral replacement device of this invention is shown, with the device being shown to be implanted on the spine.

As before, a pair of first and second transverse plates 20a, 22a engage the ends of a tubular cage 12a, and also press with their other faces against intact adjacent vertebral bodies 14a, 16a, all in a manner similar to the previous embodiment.

Transverse plates 20a, 22a each engage a single vertebral attachment plate 46, instead of a pair of vertebral attachment plates as in the last embodiment. Vertebral attachment plate 46 extends basically parallel to the spine as in the previous embodiment, and has pairs of bone screw attachment holes 34a for attachment at the respective ends of vertebral attachment plate 46 to intact, adjacent vertebral bodies 14a, 16a.

Two different modes of attachment for the transverse plates 20a, 22a and the vertebral attachment plate 46 are shown. Transverse plate 20a simply connects in a pressure connection to opposed edges of vertebral attachment plate 46 as shown. Particularly, the ends 48 of plate 20a press against vertebral attachment plate 46 with spring pressure. Thus, plate 20a can slide up and down the vertebral attachment plate 46 as may be desired for best positioning.

Alternatively, as shown with respect to transverse plate 22a, the same spring pressure attachment to vertebral attachment plate 46 may be used, but with a strap 50 extending across the ends of transverse plate 22a, with retention screws 52 being used to hold strap 50 and plate 22a together. Thus cage 12a is strongly held in a desired lateral position by the secured plate 22a.

As a further alternative, a cover plate similar to cover plate 38 may be used instead of strap 50 by the simple expedient of providing an enlarged, central section to strap 50 to cover the respective end of vertebral attachment plate 46. Thus, screw holes 34a may be covered to prevent accidental, unintended back-out of the bone retention screws, in a manner similar to the previous embodiment.

Typically, the same design for retention will be used at each end of vertebral attachment plate 46, with the different retention systems here being shown for purposes of illustration.

Transverse plate 22a can also slide up and down the vertebral attachment plate to a desired position until tightly secured, so that the system of this invention has very substantial dimensional tolerance, and thus can be used with a variety of patients.

Figure 5:
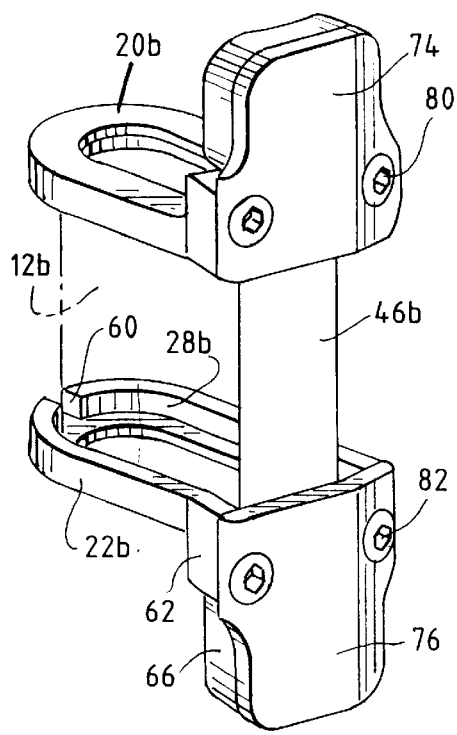
FIG. 5 is a perspective view, with the cage shown as a dotted line, of another embodiment of the spinal replacement device of this invention.
Figure 6:
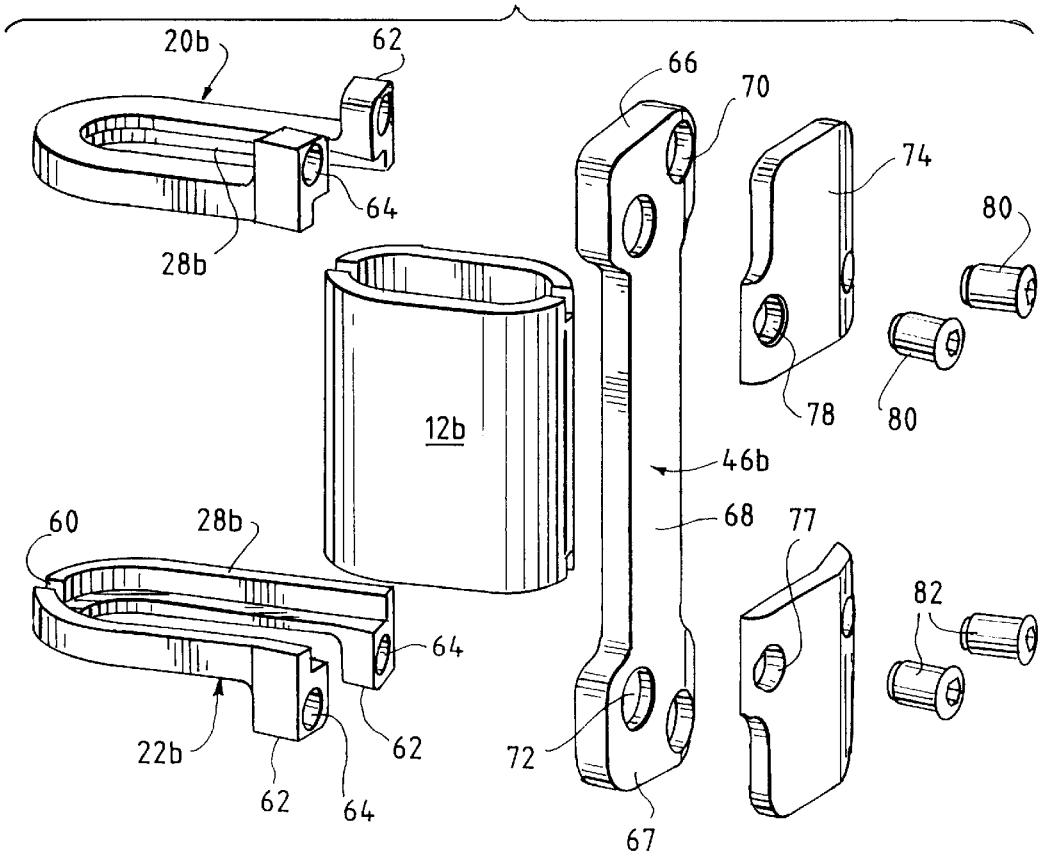
FIG. 6 is an exploded view of the spinal replacement device of FIG. 5, including the cage.

Referring to FIGS. 5 and 6, another embodiment of the spinal replacement device comprises a pair of transverse plates 20b, 22b, similar in overall concept to transverse plates 20, 22 and for a similar purpose. Each of plates 20b, 22b, may be of substantially identical design, having a peripheral upstanding wall 28b and an end aperture 60 for access of a distractor tool, similar to the corresponding end apertures in plates 20, 22. Transverse plates 20b, 22b are generally U-shaped, ending in projections 62 which each define a screw hole 64.

A vertebral attachment plate 46b is present, having end portions 66, 67, which are transversely enlarged relative to a central portion 68 between the end portions. Each of end portions 66, 67 respectively define screw apertures 70, 72 to permit attachment of plate 46b to separate vertebrae at each end of plate 46b, by bone screws (not shown) respectively passing through screw holes 70 to engage one vertebrae and screw holes 72 to engage the other vertebrae.

Cover plates 74, 76 can close off and protect the respective bone screws in apertures 70, 72, also serving to prevent backout of the bone screws from a more advanced, bone-retaining position. However, plates 74, 76 also serve to respectively retain transverse, apertured plates 20b, 22b. Screw holes 78 of cover plate 74 can engage screw holes 64 of transverse plate 20b to retain plate 20b in firm engagement with vertical attachment plate 46b, with screws 80. Screws 80 do not pass through any aperture in vertical attachment plate 46b. Rather, they pass along the central, narrower portion 68 of plate 46b, on each side thereof, being prevented from sliding off by the transversely enlarged end portions 66, 67. Thus, transverse plate 20b is securely retained to vertical attachment plate 46b, but is in a slidable relationship therewith for fine adjustment of the system with respect to the vertebrae and also with respect to cage member 12b, which maybe similar in structure and function to cage 12, or may comprise apiece of bone as previously discussed. As with previous embodiments the cover plates 74, 76 have a peripheral portion that matches and lies against a periphery portion of the vertebral attachment plate 46b.

Similarly, transverse plate 22b may be attached to cover plate 76 through the penetration of screws 82 extending through apertures 77 and 64, for retention of cover plate 76 and transverse plate 22b together in a position on vertebral attachment plate 46b within the enlarged end portions 66, 67 and prevented from sliding off plate 46b by the enlargement of portions 66, 67.

FIG. 5 shows the assembled spinal replacement device, which may be positioned in relation to the spine in a manner similar to the previous embodiments, as particularly shown in FIGS. 2, 3 and 4. The vertical positioning of transverse plates 20b, 22b along the spine is governed by the presence of cage 12b (shown in dotted lines in FIG. 5) and the respective vertebrae analogous to vertebrae 14a, 16a in FIG. 4. Thus, without being immovably fixed on vertebral attachment plate 46b, transverse plates 20b, 22b are held in an optimum position, with their spacing along vertebral attachment plate 46b being governed at least in part by the geometry of cage 12b and the positioning of the adjacent vertebrae portions analogous to 14a and 16a. Positional adjustments can spontaneously take place as needed, while collapse of the spine is prevented.

Figure 7:
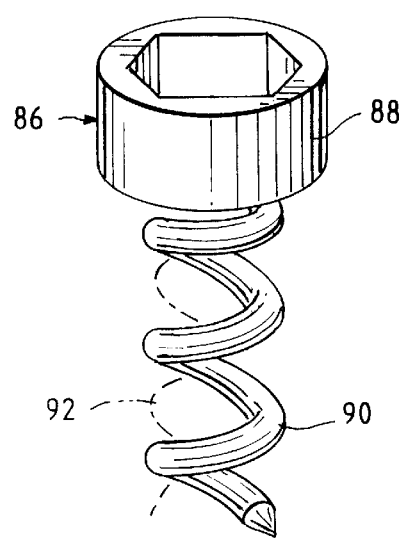
FIG. 7 is a perspective view of an open, helical bone screw which may be used in conjunction with the spinal replacement device of this invention.

Referring to FIG. 7, one embodiment of an open, helical screw of the type previously described is shown. Such screws are desirably used in each of the disclosed embodiments to secure the vertebral replacement device to at least a pair of vertebrae in the spine. For example, such screws will be used in the embodiment of FIG. 4 to pass through holes 34a, to secure the entire device to the spine. In FIGS. 5 and 6, such helical screws will pass through holes 70, 72 of plate 46b for the same purpose of adherence to the spine, to achieve a system which exhibits advantages as described above. Similarly in FIG. 2, such helical screens may extend through holes 33.

Open helical screw 86 is just one embodiment of open helical screws which maybe utilized in this invention. This particular embodiment carries a screw head 88 and a single, open helical screw shaft 90. If desired, more than one helical shaft maybe provided, as indicated by the presence of a second, optional helical shaft 92, shown diagrammatically as a helical, dotted line which is approximately 180° out of rotational phase with helical shaft 90. Similarly, if desired, three or four such helical shafts may be provided, with the helices of said shafts being preferably in coaxial relation with each other. The shape of head 88 and the shape of the shaft cross section may vary.

The above has been offered for illustrative purposes only, and is not intended to limit the scope of the invention of this application, which is as defined in the claims below.

That which is claimed:

1. An implantable spinal vertebral replacement device, which comprises:

a tubular cage for fitting into a space of a missing or damaged vertebral body;

first and second transverse plates, at least one said plate being separate from said tubular cage, said plates being respectively positioned at opposed ends of the tubular cage in a position supporting the respective cage ends, and for pressing a plate face against an adjacent vertebral body in spinal column-supporting relation, said transverse plates each defining a central aperture, said transverse plates each engaging in transverse relation to a single vertebral attachment plate, which, in use, extends generally parallel to the spine, said vertebral attachment plate defining screw holes for screw securance to a pair of vertebral bodies adjacent to said space, and in which a central, open space extends between the apertures of the first and second plates and through said cage to facilitate bone growth between said adjacent vertebral bodies through said cage, said vertebral attachment plate having end portions which are transversely enlarged relative a central portion between said end portions, at least one cover plate covering at least some of said vertebral attachment plate, said transverse plates being each transversely joined to said vertebral attachment plate by retention members that respectively connect between said transverse plate and said at least one cover plate, while extending past said vertebral attachment plate without penetrating said vertebral attachment plate.

2. The spinal replacement device of claim 1 in which said cover plate also covers said screw holes of said vertebral attachment plate for screw securance to a vertebral body, with screws occupying said screw holes.

3. The spinal replacement device of claim 2 in which said screws are of the open helix type.

4. The spinal replacement device of claim 1 in which said cage is of non-circular cross section.

5. The spinal replacement device of claim 4 in which said cage comprises a bone having ends of non-circular cross section which are secured in said transverse plates, and a lumen extending therethrough from end to end.

6. The spinal replacement device of claim 1 in which a portion of the cover plate periphery matches and lies against a portion of the periphery of the vertebral attachment plate.

7. The spinal vertebral replacement device of claim 1 in which at least one transverse plate can slide up and down the vertebral attachment plate to a desired position, so that the system has substantial dimensional tolerance and can be used with a variety of patients.

8. An implantable spinal vertebral replacement device, which comprises:

a tubular cage for fitting into a space of a missing or damaged vertebral body;

first and second transverse plates, at least one said plate being separate from said tubular cage, said plates being respectively positioned at opposed ends of the tubular cage in a position supporting the respective cage ends, and for pressing a plate face against an adjacent vertebral body in spinal column-supporting relation, said transverse plates each defining a central aperture, said transverse plate each engaging in transverse relation to a single vertebral attachment plate, which, in use, extends generally parallel to the spine, said vertebral attachment plate defining screw holes for screw securance to a pair of vertebral bodies adjacent to said space, with screws of the open helix type occupying said screw holes, and in which a central, open space extends between the apertures of the first and second plates and through said cage to facilitate bone growth between said adjacent vertebral bodies through said cage, said vertebral attachment plate having end portions which are transversely enlarged relative to a central portion between said end portions, at least one cover plate covering at least some of said vertebral attachment plate, said transverse plates being each transversely joined to said vertebral attachment plate by retention members that respectively connect between said transverse plate and said at least one cover plate, while extending past said vertebral attachment plate at a position between said transversely enlarged end portions and without penetrating said vertebral attachment plate, further in which said cover plate also covers said screw holes and open helix type screws of said vertebral attachment plate.

9. The spinal replacement device of claim 8 in which said cage is of non-circular cross section.

10. The spinal replacement device of claim 9 in which said cage comprises a bone having ends of non-circular cross section which are secured in said transverse plates, and a lumen extending therethrough from end to end.

11. The spinal replacement device of claim 9 in which a portion of the cover plate periphery matches and lies against a portion of the periphery of the vertebral attachment plate.

12. The spinal vertebral replacement device of claim 11 in which at least one transverse plate can slide up and down the vertebral attachment plate to a desired position, so that the system has substantial dimensional tolerance and can be used with a variety of patients.

13. An implantable spinal vertebral replacement device, which comprises:

a tubular cage of noncircular cross section for fitting into a space of a missing or damaged vertebral body;

first and second transverse plates, said plates being respectively positioned at opposed ends of the tubular cage in a position supporting the respective cage ends, and for pressing a plate face against an adjacent vertebral body in spinal column-supporting relation, said transverse plates each defining a central aperture, said transverse plates each engaging in transverse relation to a vertebral attachment plate which, in use, extends generally parallel to the spine, said vertebral attachment plate defining screw holes for spinal securance;

screws of the open helix type occupying said screw holes for said spinal securance, in which a central, open space extends between the apertures of the first and second plates and through said cage to facilitate bone growth between said adjacent vertebral bodies through said cage.

14. The spinal replacement device of claim 13 in which at least one cover plate covers at least a portion of said vertebral attachment plate and the screw holes in said vertebral attachment plate for screw securance to a vertebral body, with said screws occupying said screw holes.

15. The spinal replacement device of claim 13 in which a portion of said cover plate periphery matches and lies against a portion of the periphery of the vertebral attachment plate.

16. The spinal replacement device of claim 13 in which said cage comprises a bone having ends of non-circular cross section which are secured in said transverse plates, and a lumen extending therethrough from end to end.

* * * * *